United States Patent [19]

Frey et al.

[11] Patent Number: 4,777,942
[45] Date of Patent: Oct. 18, 1988

[54] BONE MILLING INSTRUMENT

[75] Inventors: Otto Frey; Kurt Bider, both of Winterthur, Switzerland

[73] Assignee: Sulzer Brothers Limited, Winterthur, Switzerland

[21] Appl. No.: 100,599

[22] Filed: Sep. 24, 1987

[30] Foreign Application Priority Data

Oct. 2, 1986 [CH] Switzerland .................. 3937/86

[51] Int. Cl.⁴ .............................. A61F 5/04
[52] U.S. Cl. .................. 128/92 VJ; 409/178
[58] Field of Search ............... 128/92 VJ, 83, 303 R, 128/92 V, 305; 409/175, 178, 179; 433/51, 76

[56] References Cited

U.S. PATENT DOCUMENTS

| 272,648 | 2/1984 | Bolesky et al. | 128/92 VJ X |
| 273,806 | 5/1984 | Bolesky et al. | 128/92 VJ X |
| 4,306,550 | 12/1981 | Forte | 128/92 VJ |
| 4,466,429 | 8/1984 | Loscher et al. | 128/92 VJ |
| 4,474,177 | 10/1984 | Whiteside | 128/92 VW |
| 4,541,423 | 9/1985 | Barber | 128/92 V |
| 4,587,964 | 5/1986 | Walker et al. | 128/92 VJ |
| 4,706,659 | 11/1987 | Mathews et al. | 128/83 X |

FOREIGN PATENT DOCUMENTS 2356464  5/1975  Fed. Rep. of Germany ... 128/92 VJ

Primary Examiner—Robert A. Hafer
Assistant Examiner—Kevin G. Rooney
Attorney, Agent, or Firm—Kenyon & Kenyon

[57] ABSTRACT

The milling instrument has a caliper which is inserted into a medullary cavity and a spindle which is linked to the caliper at an angle. The spindle carries a milling cutter as well as a guide shoe at the distal end which slides within a guideway at the distal end of the caliper. The instrument is able to cut a circular arc corresponding to the boundary line between the spongiosa and cortical tissue in the region of the calcar arc.

13 Claims, 1 Drawing Sheet

U.S. Patent    Oct. 18, 1988    4,777,942
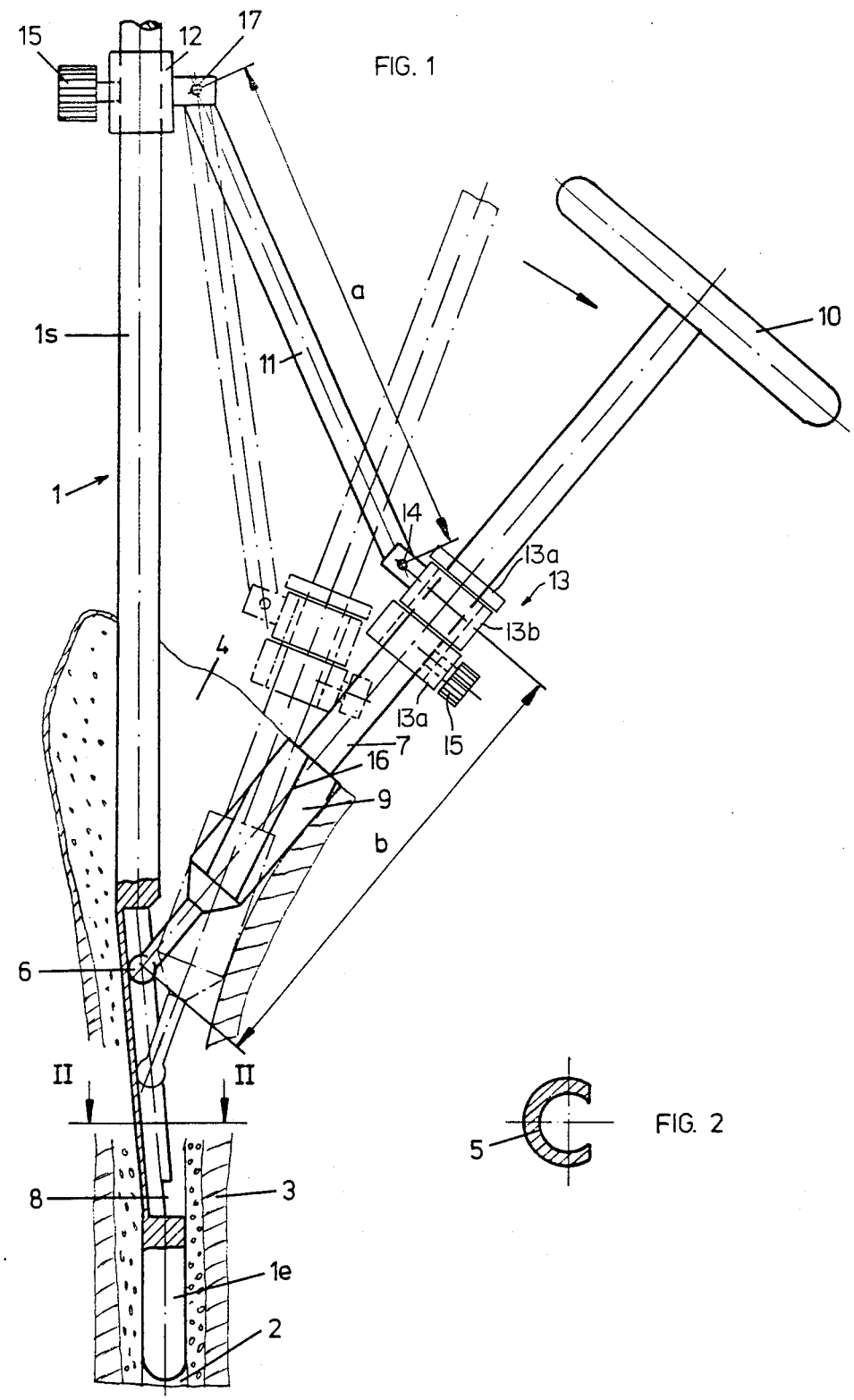

BONE MILLING INSTRUMENT

This invention relates to a bone milling instrument. More particularly, this invention relates to a bone milling instrument for milling curves in femurs.

Heretofore, various types of milling instruments have been known for the milling of hollow spaces within a femur. For example, German No. PA2356464 describes a milling instrument with calipers which can be placed into a bore extending in a longitudinal direction of a medullary cavity in order to mill out a triangular hollow space bounded by straight lines in the region of the neck of the femur. However, this known instrument does not permit routing out of an arc-shaped area which, for example, corresponds to the "Boundary Line" between the spongiosa and the cortical tissue in the region of the calcar arc.

Accordingly, it is an object of the invention to provide a bone milling instrument which is capable of milling an arc in a femur in the region of the calcar arc of the femur.

It is another object of the invention to be able to precisely and exactly mill an arc in a femur in the region of the calcar arc.

Briefly, the invention provides a bone milling instrument comprised of a caliper for insertion in a medullary cavity of a femur and a rotatable spindle which is linked to the caliper. In addition, the caliper is provided with a longitudinal guideway adjacent a distal end while the spindle has a distal end slidedly mounted in the guideway as well as a milling cutter thereon for milling in an area of a calcar arc of the femur.

When in use, the spindle can be rotated so that the milling cutter is able to mill in the region of the calcar arc. At the same time, the spindle can be guided within the guideway of the caliper so that a curved surface can be milled within the the femur as the distil end of the spindle is moved along the caliper, i.e. in the proximal direction.

The guide motion of the instrument is carried out essentially in the direction of the longitudinal axis of the instrument. With this motion, an arc-shaped boundary of the milled out hollow space can be created.

The instrument is also provided with a means linking the spindel to the caliper in order to dispose the spindle at an inclined angle relative to the caliper. For example, this means may include a bar which is pivotally connected at one end to the caliper and pivotally connected at the opposite end to the spindle. Still further, the bar can be connected at each end to the respective caliper and spindle via a slide box which is adjustably mounted longitudinally of the respective caliper and spindle. This permits the shape of the arc, and primarily the radius of the arc, to be made variable. That is, by adjusting the respective slide boxes along the caliper and/or spindle, the arc may be varied during milling.

Alternatively, the bar of the linkage means can be removably mounted and exchanged for a bar of greater or less length so as to vary the shape of the arc being milled.

In order to facilitate fixation of the caliper in the bore of the medullary cavity of the bone, the guideway is inclined relative to the longitudinal axis of the caliper. This displaces the axis of the distal end of the caliper laterally relative to a stem of the caliper located on the opposite side of the guideway and facilitates placement of the caliper on the bone in the region of the greater trochanter.

These and other objects and advantages of the invention will become apparent from the following detailed description taken in conjunction with the accompanying drawings wherein:

FIG. 1 illustrates a side view of an instrument constructed in accordance with the invention within a femur shown in longitudinal section; and FIG. 2 illustrates a view taken on line II—II of FIG. 1.

Referring to FIG. 1, the bone milling instrument includes a caliper 1 which is sized for insertion in a medullary cavity 2 of a femur 3. As indicated, the caliper 1 has a distal end 1e and a stem 1s each of which is disposed on a longitudinal axis which is displaced laterally of each other. In addition, a longitudinally extending guideway 5 extends between the distal end 1e and the stem 1s angularly of the stem 1s. The proximal end of the stem 1s terminates in a handle (not shown).

The displacement of the caliper stem 1s from the distal end 1e permits the stem 1s to lie against the bone tissue in the region of the greater trochanter even though a surgical opening 4 created in the spongiosa is laterally displaced relative to the central cavity or bore 2 in the femur 3.

Referring to FIGS. 1 and 2, the guideway 5 is formed in a hollow portion of the caliper 1 and has a C-shaped cross section.

The milling instrument also includes a spindle 7 which is linked to the caliper 1. As indicated, the spindle 7 has a spherical guide shoe 6 at the distal end which is slideably and rotatably mounted in the guideway 5. This guide shoe 6 can be "threaded" into the guideway 5 through an enlarged C-shaped opening 8 at the lower end of the guideway 5. The spindle 7 also has a milling cutter 9 thereon for milling in an area of the calcar arc of the femur 3. This cutter 9 may be slid onto the spindle 7 from the distal end and held in place, for example, by means of two clamping screws (not shown) which pass radially through the cutter 9 into the spindle 7. Alternatively, the cutter 9 may be soldered at the upper face to the spindle 7. In addition, the cutter 9 includes a plurality of milling edges 16 as is known while the spindle 7 carries a handle 10 at the proximal end for rotation of the spindle 7.

Referring to FIG. 1, the spindle 7 is linked to the caliper 1 by a means which disposes the spindle 7 at an inclined angle relative to the caliper 1 while permitting the angle of inclination to change as the spindle 7 slides upwardly within the guideway 5, as viewed. The means for linking the spindle 7 to the caliper 1 includes a bar 11 which is pivotally connected at one end about a pivot axis 17 to the caliper 1 via a slide box 12 and pivotally connected at the opposite end about a pivot axis 14 to a slide box 13 on the spindle 7. Each slide box 12, 13 is adjustably mounted longitudingly of the respective caliper 1 and spindle 7. Further, the slide box 12 is clamped to the stem 1s via a knurled screw 15. The slide box 13 is composed of an inner sleeve 13a which can slide longitudinally on the spindle 7 and is fixable thereon by clamping with a further knurled screw 15 and of an outer sleeve 13b rotatably mounted on the inner sleeve 13a. This outer sleeve 13b bears the pivot axis 14, as shown.

As indicated, the bar 11 is of a given length a. In addition, the bar 11 is removably mounted on each slide box 12, 13 in order to be replaced from time to time by a bar of a different length, for example, to change the arcuate shape of the milled bone. The distance between the pivot axis 14 and the point of intersection of the guide shoe 6 to the axis of the guideway 5 represents a second "link" of a length b.

Variations in the lengths of the links a, b as well as sliding of the slide box 12 on the caliper stem 1s changes the shape and position of the milled arc, that is, primarily the radius of the arc, as well as the height of the arc relative to a point of reference, for example the "tip" of the greater trochanter.

In order to use the instrument, the following procedure is suggested.

After resecting the joint head, the bore or medullary cavity 2 is initially generated following conventional procedures. Subsequently, in a oustomary manner, the hollow space 4 is created in the spongiosa with a rasp. Before inserting the instrument, the approximate course of the arc of the "boundary line" between spongiosa and corticalis in the area of the calcar arc is determined by X-rays. On the basis of the determined shape of the arc, the length of the bar 11 and the position of the pivot axis 14 on the spindle 7 are set, and thus, the values a and b. The ratio of a and b is maintained at a constant throughout the surgical procedure.

After the distal end 1e of the caliper 1 has been inserted in the bore 2, the stem 1s is braced against the lateral boundary, that is, the boundary of the hollow space 4 pointing to the greater trochanter. The spindle 7 with the milling cutter 9 is then brought into the deepest position at which the cutter 9 is intended to start cutting the "innermost" part of the arc. In this position, the guide shoe 6 is in its lowest working position. By turning the handle 10, the spongiosa is peeled off by the milling edges 16 of the outer wall of the cutter 9 with the deepest regions of the edges 16 put into action first.

By moving the spindle 7 from the position indicated by the dashed lines in FIG. 1 to the position indicated by solid lines, the guide shoe 6 travels upwardly within the guide way 5. At the same time, the arc shape of the milled out region is generated since, with the upward movement of the cutter 9, the "cutting region" on its outer wall also travels upwardly by placing different outer wall heights of the cutter 9 against the bone 3 in the positions indicated by dashed and solid lines.

Using the above procedure, a circular arc can be cut in the femur 3 which at least approximately corresponds to the "boundary line" between spongiosa and cortical tissue in the region of the calcar arc.

In the event that the arc which is to be milled is different from a previous arc, the bar 11 can be replaced by a bar of greater or less length. Alternatively, the positions of the guide shoes 12, 13 on the caliper 1 and spindle 7, respectively can be adjusted.

Of note, since the spindle 7 rotates, suitable means are provided within the guide shoe 13 to accommodate the rotation of the spindle 7.

The invention thus provides a bone milling instrument which is able to mill out an arc in a femur precisely and exactly. Further, the instrument can be manipulated in a relatively easy manner.

What is claimed is:

1. A bone milling instrument comprising
a caliper having a distal end for insertion in a medullary cavity of a femur and a longitudinally extending guideway;
a spindle having a guide shoe at a distal end slidably mounted in said guideway and a milling cutter thereon for milling a curve in an area of a calcar arc of the femur; and
means linking said spindle to said caliper to dispose said spindle angularly relative to said caliper.

2. A bone milling instrument as set forth in claim 1 wherein said caliper has a stem disposed on a longitudinal axis and said guideway is disposed angularly of said stem between said distal end and said stem.

3. A bone milling instrument as set forth in claim 1 wherein said means is adjustable.

4. A bone milling instrument as set forth in claim 1 wherein said means includes a bar pivotally connected at one end to said caliper and pivotally connected at an opposite end to said spindle.

5. A bone milling instrument as set forth in claim 4 wherein said means further comprises a first slide box adjustably mounted longitudinally of said caliper and pivotally connected to said one end of said bar and a second slide box adjustably mounted longitudinally of said spindle end pivotally connected to said opposite end of said bar.

6. A bone milling instrument as set forth in claim 4 wherein said bar is removably connected to said caliper and said spindle.

7. A bone milling instrument comprising
a caliper for insertion in a medullary cavity of a femur, said caliper having a longitudinally extending guideway adjacent a distal end; and
a rotatable spindle having a distal end slidably mounted in said guideway and a milling cutter thereon for milling in an area of a calcar arc of the femur.

8. A bone milling instrument as set forth in claim 7 which further comprises a bar pivotally connected at one end to said caliper and pivotally connected at an opposite end to said spindle to link said spindle to said caliper.

9. A bone milling instrument as set forth in claim 7 which further comprises a first slide box adjustably mounted longitudinally of said caliper and pivotally connected to said one end of said bar and a second slide box adjustably mounted longitudinally of said spindle and pivotally connected to said opposite end of said bar.

10. A bone milling instrument as set forth in claim 9 wherein said caliper has a stem disposed on a longitudinal axis and said guideway is disposed angularly of said stem between said distal end and said stem.

11. A bone milling instrument as set forth in claim 7 wherein said caliper has a stem disposed on a longitudinal axis and said guideway is disposed angularly of said stem between said distal end and said stem.

12. A bone milling instrument as set forth in claim 7 wherein said spindle has a spherical guide shoe at said distal end for sliding and rotating in said guideway.

13. A bone milling instrument as set forth in claim 8 wherein said bar is removably connected to said caliper and said spindle.

* * * * *

UNITED STATES PATENT AND TRADEMARK OFFICE
CERTIFICATE OF CORRECTION

PATENT NO. : 4,777,942

DATED : Oct. 18, 1988

INVENTOR(S) : OTTO FREY, et al

It is certified that error appears in the above-identified patent and that said Letters Patent is hereby corrected as shown below:

Column 1, line 31 "slidedly" should be -slidingly-
Column 1, line 39 "the the" should be -the-
Column 2, line 57 "longitudingly" should be -longitudinally-
Column 3, line 16 "oustomary" should be -customary- Signed and Sealed this Eighteenth Day of April, 1989

Attest:

DONALD J. QUIGG

*Attesting Officer*  Commissioner of Patents and Trademarks